United States Patent [19]

Mok

[11] Patent Number: 4,641,650
[45] Date of Patent: Feb. 10, 1987

[54] PROBE-AND-FIRE LASERS

[75] Inventor: Walter Y. W. Mok, Palo Alto, Calif.

[73] Assignee: MCM Laboratories, Inc., Mountain View, Calif.

[21] Appl. No.: 710,431

[22] Filed: Mar. 11, 1985

[51] Int. Cl.$^4$ ............................................. A61B 17/35
[52] U.S. Cl. ................................. 128/303.1; 128/665; 128/6
[58] Field of Search ....................... 128/4–8, 128/303.1, 395–398, 664, 665; 219/121 LA, 121 LB; 358/78; 370/30

[56] References Cited

U.S. PATENT DOCUMENTS

| Re. 31,815 | 1/1985 | Alfaro | 128/665 |
|---|---|---|---|
| 4,207,874 | 6/1980 | Choy | 128/6 |
| 4,266,549 | 5/1981 | Kimura | 128/665 |
| 4,316,467 | 2/1982 | Muckerheide | 128/303.1 |
| 4,336,809 | 1/1982 | Clark | 128/665 |
| 4,418,688 | 12/1983 | Loeb | 128/6 |
| 4,438,765 | 3/1984 | Wilinsky | 128/303.1 |
| 4,454,882 | 1/1984 | Takano | 128/6 |
| 4,550,240 | 10/1985 | Toida et al. | 128/303.1 |
| 4,556,057 | 12/1985 | Hiruma et al. | 128/303.1 |
| 4,576,177 | 3/1986 | Webster | 178/303.1 |

FOREIGN PATENT DOCUMENTS

| 2517129 | 6/1976 | Fed. Rep. of Germany | 128/665 |
|---|---|---|---|
| 0097788 | 6/1984 | Japan | 219/121 LA |

Primary Examiner—Edward M. Coven
Assistant Examiner—Max F. Hindenburg

[57] ABSTRACT

Method and apparatus of irradiating a treatment area within a body includes introducing elongated flexible radiation transfer conduit (fiberoptic arrays) into the body cavity with the distal end thereof operatively opposite the treatment area. At the other end of the conduit there is photoelectrically sensed a particular optical characteristic of the treatment area (such as fluorescence) and as long as the particular optical characteristic is sensed there is periodically transmitted laser pulses via the conduit to the treatment site.

8 Claims, 5 Drawing Figures

LASER SURGERY SYSTEM

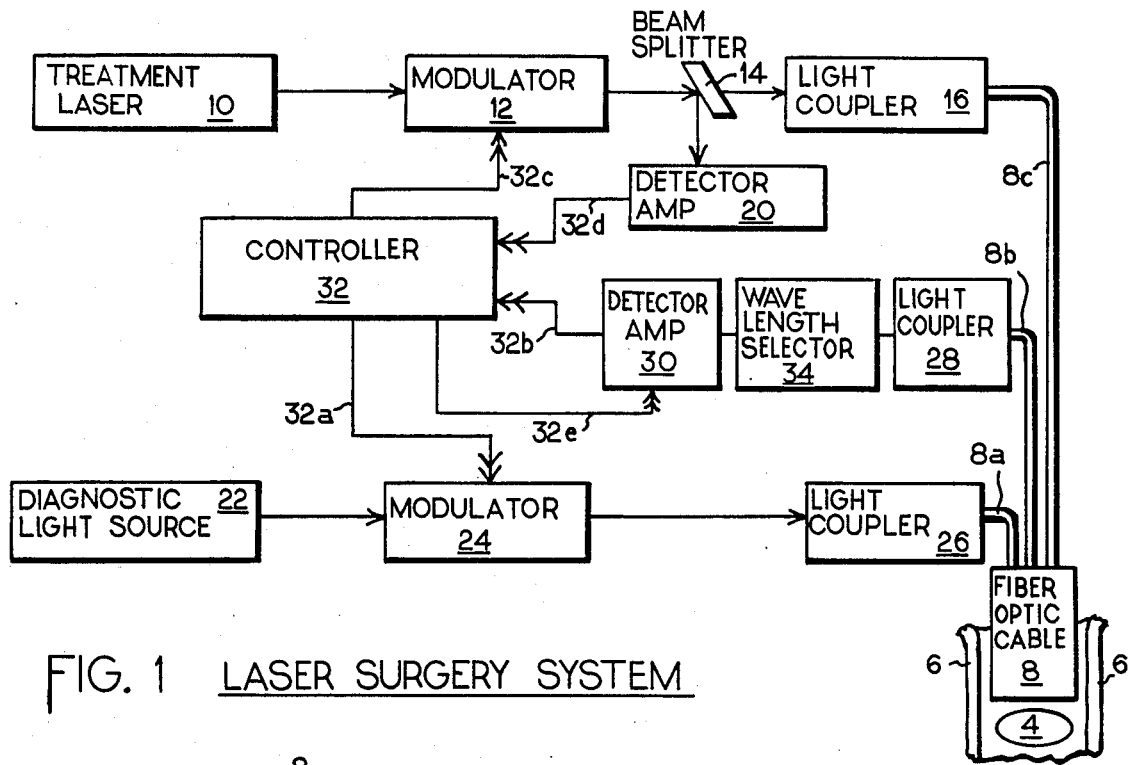
FIG. 1  LASER SURGERY SYSTEM
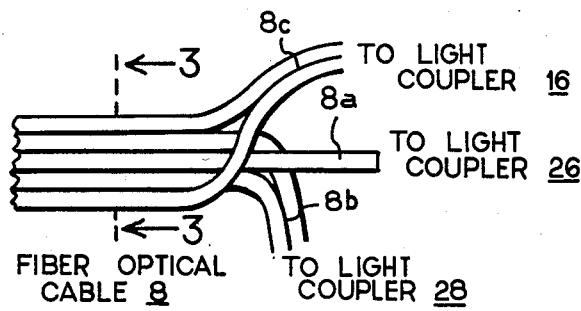
FIG. 2
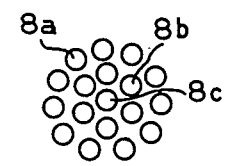
FIG. 3
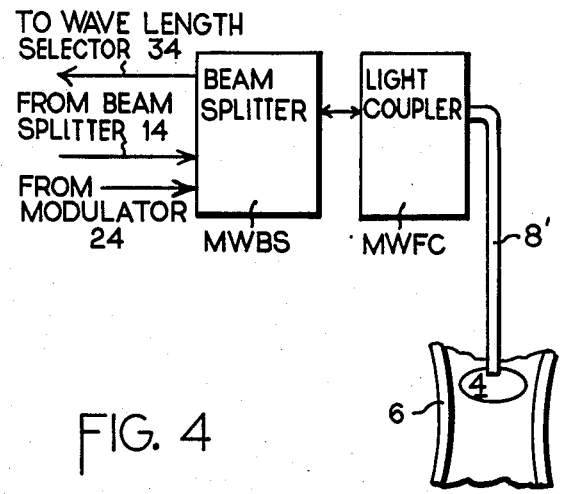
FIG. 4
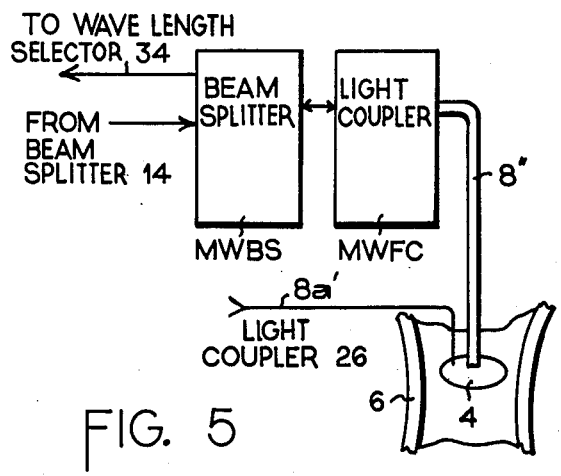
FIG. 5

PROBE-AND-FIRE LASERS

FIELD OF INVENTION

This invention pertains to the use of lasers in medicine and, more particularly, to the controllable firing of medical lasers when performing surgery.

DISCUSSION OF PRIOR ART

Currently, medical and surgical laser output is guided visually by the operator. The eye, or an optical viewing device, is used to identify the treatment area and fire the laser. A major problem is that imperfect visualization of the treatment area leads to poor aim of the laser and consequently to damage of healthy tissue adjacent to the treatment area. When the laser device is accurately aimed, it is still difficult for the operator to know precisely the amount of laser energy to be delivered to destroy the treatment area without damaging the underlying tissue. Oversupply of laser energy may lead to an irreversible destruction of healthy tissue around the treatment site. This destruction can lead to side effects and complications from the procedure. Undersupply of laser energy may lead to inadequate destruction of the treatment area and a therapeutic failure. Furthermore, the problem is complicated because of the diversity of tissue types that are potential lesions.

U.S. Pat. No. 4,438,765 teaches the use of a laser surgical device wherein the controlling of the firing of the laser is by a motion detector to ensure that there is no movement of, say, the eyeball when the laser is fired for retinal fusion.

U.S. Pat. No. 4,316,467 teaches the use of a laser in removing naturally pigmented tissue from the skin. The firing of the laser is controlled by the color of the treatment area sensed by a photodetector. Both of these patents are basically concerned with the use of a laser in the surgical treatment of external body surfaces.

In order to enhance the visualization of the treatment area, there have been developed certain dyes which can selectively stain the diseased tissue. The difference in the optical property of the stained tissue and the unstained healthy tissue improves the visualization of the treatment area. U.S. Pat. No. 4,336,809 is typical of the teaching of a photoradiation method for tumor enhancement with hematoporphyrin dye, wherein the dyed lesion site is bathed with radiation of a particular wavelength to cause it to fluoresce.

When dealing with lesion sites within the body cavity, it is necessary to deliver the laser energy internally to the lesion site. U.S. Pat. Nos. 3,858,577 and 4,273,109 are typical of fiberoptic light delivery systems.

In spite of all of this existing technology, there is still not available a laser surgical system which is capable of performing laser surgery within the body cavity such that the laser effects are automatically monitored to control the output of the laser and to terminate its operation before there is a destruction of healthy tissue around the treatment site.

BRIEF SUMMARY OF THE INVENTION

It is, accordingly, a general object of the invention to provide an improved method of delivering laser energy for the treatment of an area within a body cavity.

It is a more specific object of the invention to provide such laser energy only as long as the treatment area shows the need for such laser energy and to terminate the application of the laser energy when the malignant portion of the treatment has been destroyed.

Accordingly, with this aspect of the invention, there is provided a method for radiating a treatment area within a body cavity by introducing an elongated flexible radiation transfer conduit into the body cavity until the distal end thereof is operatively opposite the treatment area.

There is a particular optical characteristic of the treatment area which is photoelectrically sensed and as long as this optical characteristic is sensed, laser pulses are periodically transmitted into the proximal end of the conduit for transfer to the distal end and the treatment site.

In accordance with a feature of the invention, if the treatment area has no inherent optical properties which are sufficiently different from the surrounding healthy tissue, then before the treatment begins there is introduced into the treatment area a reagent which will cause the treatment area to be characteristically stained so that when the photoelectric sensing takes place the optical properties of the characteristic staining will be sensed.

According to a specific feature of the invention, there is contemplated a method of destroying atheromatous plaque within an a rtery of a patient comprising the steps of initially administering to the patient a non-toxic atheroma-enhancing reagent which causes plaque to have a characteristic optical property when illuminated with a given radiation. Thereafter, a catheter system including fiberoptical cable means is introduced into the artery such that the distal end thereof is operatively opposite the plaque site. There is then introduced into the proximal end of the fiberoptical cable the given radiation. When plaque is illuminated with the given radiation, a characteristic optical property is sensed at the proximal end. There is then fed via the cable means from the proximal end to the distal end periodically occurring laser pulses until the characteristic optical property is no longer sensed.

In order to implement the method of the invention, there is contemplated a laser system having fiberoptical bundle with a central optical diagnostic means, a receiving fiberoptical array means annularly disposed about the diagnostic means and a treatment fiber optical array means annularly disposed about the receiving fiberoptical array means. A treatment laser source is connected to one end of the treatment fiberoptical array means, a diagnostic light source is connected to a corresponding end of the central fiberoptical diagnostic means and a radiation detector is connected to the corresponding end of the receiving optical fiber means.

Another implementation of the method of the invention contemplates the use of a single optical fiber which transmits time multiplexed radiation. A further implementation contemplates two fibers, one handling diagnostic radiation and the other multiplexed treatment and sensed radiation.

BRIEF DESCRIPTION OF THE DRAWINGS

Other objects, the features and advantages of the invention will be apparent from the following detailed description when read with the accompanying drawing in which:

FIG. 1 is a block diagram of a laser system utilizing the invention;

FIG. 2 is a schematic longitudinal section of the fiber optic cable of the system of FIG. 1;

FIG. 3 is a cross-sectional view of said cable along the lines III—III of FIG. 2;

FIG. 4 is a block diagram of a portion of the laser system of FIG. 1 utilizing a single optical fiber; and FIG. 5 is a block diagram of a portion of the laser system of FIG. 1 utilizing two optical fibers.

DETAILED DESCRIPTION OF THE PREFERRED EMBODIMENTS OF THE INVENTION

The invention will be described utilizing the example of the destruction of an atheromatous plaque 4 from the artery 6 of FIG. 1. Initially, the patient is administered a dose of a dye to enhance the contrast between the treatment site (plaque) and the healthy surrounding tissue. A typical dye is tetracycline which has the property of fluorescing when radiated with an ultraviolet light. This dye has a special property of accumulating within the plaque relative to normal healthy tissue. Therefore, a predetermined time after the administration of the dye, the fiberoptic cable 8 is inserted into the artery with the distal end thereof opposite the treatment site. The optical cable 8 in a first embodiment (see also FIGS. 2 and 3) includes a central optical fiber 8a coupled to the output of light coupler 26, an annular array of optical fibers 8b surrounding the central fiber 8a connected to the input of light coupler 28, and an outer annular array of cables of fibers 8c is coupled to the output of light coupler 16. Light coupler 26, of conventional design, receives light from the diagnostic light source 22 via the optical modulator 24. Diagnostic light source 22 for the present example would be a source of ultraviolet light. If other dyes were used, then appropriate light sources for those dyes would be selected. The light indicated by the single arrowhead line feeds the input of modulator 24 whose output is fed to the input of coupler 26. The modulator 24 can be of a conventional opto-accoustic modulator or an electromechanical shutter which passes or blocks the light in response to an electrical signal from controller 32 (note all electrical signal lines show double arrowheads). Thus, the presence or absence of a signal on line 32a from the controller 32 can close or open the light path between diagnostic light source 22 and light coupler 26.

The proximal end of array 8b feeds light into the light coupler 28 whose output is fed into the wavelength selector 34 which selects light corresponding to the predetermined characteristic wavelength to be detected. In turn, the selected light feeds detector-amplifier 30 whose output is fed via signal lead 32b to the controller 32. The detector-amplifier 30 can be the combination of, for example, a photodiode which drives a transistor amplifier, a photomultiplier, or in and of itself can be a phototransistor. Thus, whenever light is received from array 8b, a signal will be transmitted to controller 32. The detector/amplifier 30 is controlled by signals on line 32e from controller 32.

Treatment laser 10 will transmit light to modulator 12 which is controlled by signals on line 32c from controller 32. The controlled light from modulator 12 is fed to a conventional beam spliter 14 with a portion of the light being deflected to detector/amplifier 20 and the remaining light passing to the input of light coupler 16. The output of light coupler 16 is fed to the proximal end of optical fiber array 8c. Beam splitter 14 also feds part of the beam to detector/amplifier 20 which in turn feeds a signal on line 32d to controller 32 which provides feedback sensing of the laser output to ensure constancy of the amplitude of the laser output over time.

In operation, after the dye has been inserted and the cable 8 is in place, the diagnostic light source 22 passes light via modulator 24, coupler 26 and array 8a to the treatment site 4. The plaque in the treatment site will fluoresce and the fluorescence will be picked up by the array 8b and fed to the light coupler 28 and, thence, to the wavelength selector 34. The output from the wavelength selector 34, corresponding to the characteristic fluorescent emission of tetracycline, is fed to the detector/amplifier 30 which in response will emit a signal on line 32b to controller 32. The controller 32 in response thereto will send a signal on line 32c to open the modulator 12 to emit laser energy of a predetermined power and wavelength for a set time interval. Accordingly, a pulse of light from treatment laser 10 will be fed via the beam splitter, light coupler 16 and the array 8c to the treatment area 4. Because light reflected from the treatment area can be very great during the time of the laser pulse, controller 32 via line 32e feeds a signal to detector/amplifier 30 to turn off the detector for a prefetermined time interval. This signal can also be fed to modulator 24 to prevent the radiation of ultraviolet light during the laser pulse. Controller 32 then switches signals on lines 32c and 32e at the prefetermined timing delays such that the laser output is blocked and the fluorescent light can again be sensed from the treatment site. If the fluorescence is then detected indicating that plaque is still present, the detector 30 will send a signal to controller 32 which, again, switches the signals on the lines 32e and 32c, initiating another laser pulse. This sequence continues until no fluorescence is detected indicating that all plaque has been destroyed. At that time, no signal is fed to controller 32 and no further laser pulse is generated. In this way, using the probe-and-fire technique of the invention, the possibliy of destroying healthy tissue is minimized. The controller 32 in its simplest form can dispense with the use of detector-amplifier 20 and can merely be a monostable device which is momentarily triggered on a pulse from line 32b and then reverts to its rest state. The paraphase output of this device can be connected via appropriate amplifiers to lines 32a, 32b and 32e.

To facilitate the positioning of the laser catheter within narrow tortuous pathways a single flexible optical fiber 8' (or small diameter bundle) is used (See FIG. 4) instead of the multibundle cable 8 of FIG. 1. More particularly, the light couplers 26, 28 and 16 connected to their associated bundles 8a, 8b and 8c are replaced by a single multiple-wavelength coupler MWFC which optically couples multiple-wavelength beam splitter MWBS to single optical fiber 8'. Multiple-wavelength beam splitter MWBS receives laser light from beam splitter 14 (FIG. 1) along a given incident angle path and diagnostic light from modulator 24 (FIG. 1) along another given incident angle path and transmits such received light via a port along a common transmit-receive path to multiple-wavelength light coupler MWLC. Furthermore, radiation from the treatment site 4 is fed from multiple-wavelength coupler MWLC via the comnon transmit-receive path into the port of multiple-wavelength beam splitter MWBS. This light is emitted therefrom to wavelength fitter 34 via a further path having an angle different from the two given incident path angles. Because of the nature of the multiple-wavelength beam splitter MWBS it may be possible to delete fitter 34 and feed detector/amplifier 30 directly from the beam splitter.

The so-modified system operates in the same manner as the system of FIG. 1. In FIG. 5 the fiber optical configuration is modified to a dual fiber configuration. This configuration may put less demands on the multiple-wavelength beam splitter MWBS and may permit more diagnostic light to reach the treatment site 4. In this embodiment a single fiber or bundle 8a' is connected to light coupler 26 (FIG. 1). The fiber 8" or narro diameter cable is connected to multiple-waveength light coupler MWFC which is optically-coupled via a comnon transmit-receive path to the ports of the multiple-wavelength beam splitter MWBS. Laser light is received along a given incident angle path from beam splitter 14 (FIG. 1) and fluorescent light from coupler MWFC is fed from multiple-wavelength beam splitter MWBS via an output optical path having a different angle to wavelength selector 34 (FIG. 1). As with the embodiment of FIG. 4 fitter 34 may be omitted.

Operation of the system utilizing the embodiment of FIG. 5 is the same as the other embodiments.

While only a limited number of embodiments of the invention has been shown and described in detail, there will now be obvious to those skilled in the art many modifications and variations satisfying many or all of the objects and features of the invention without departing from the spirit thereof. For example, while only the treatment of plaque has been described the invention can be used as a treatment of other diseases such as tumors(cancer), stones in urinary tract and gall bladder as well as prostate obstructions. In addition, depending on the nature of the treatment site, the appropriate dye is selected to enhance the contrast between normal tissue and malignant tissue. When the treatment site is a tumor, one can successfully use hematoporphyrin or its derivatives. In some cases, inherent differences in optical properties between the treatment site and the surrounding healthy tissue may eliminate the need for a dye. Again, depending on the treatment site and the dyes involved, the diagnostic light can be ultraviolet, infrared, white light, etc. Furthermore, again depending on the treatment site, the laser source can take many forms such as argon, Nd-yag, carbon dioxide, tunable dye, and excimer lasers with pulse or continuous output. The choice of the diagnostic light source is predicated on the optical characteristics of the dye and/or the treatment site. However, the choice of the coherent light source for the treatment laser does not have to match the absorption peak of the dye. The treatment laser can be any wavelength that destroys the diseased treatment site. Normally, there is a risk that this light will also destroy healthy tissue. However, the possibility does not exist since once the diseased treatment site is removed, the means for triggering the laser pulse is also removed.

The fiberoptic cable can be coupled with catheter designs which include, but are not limited to, such features as endoscopy, balloon devices, steerable guiding systems, multiple lumens for infusion and suctioning, ultrasonic guidance, monitoring or ablation, pressure and temperature monitoring and catheter centering devices.

What is claimed is:

1. A surgical laser system for operating on a treatment site comprising:
   a fiber optical means having a proximal end and a distal end positionable in operative proximity to the treatment site;
   a treatment laser source optically connected to the proximal end of said fiber optical means;
   a diagnostic radiation source connected to the proximal end of said fiber optical means for irradiating the treatment site;
   a responding radiation detector means connected to the proximal end of said fiber optical means for generating a control signal when detecting a particular radiation in response to being irradiated by said diagnostic radiation source from the treatment site; and
   means for controlling said treatment laser source to operate only when said radiation detector means emits said control signal.

2. The system of claim 1 wherein said fiber optical means comprises a multiple-wavelength beam splitter, a fiber optical device and a multiple-wavelength optical coupler optically coupling said multiple-wavelength beam splitter to said fiber optical device.

3. The system of claim 2 wherein said fiber optical device is a single optical fiber.

4. The system of claim 2 wherein said fiber optical device is a single bundle of optical fibers.

5. The system of claim 1 wherein said fiber optical means comprises first and second fiber optical devices, a multiple-wavelength beam splitter optically coupled to said treatment laser source and to said responding radiation detector, a multiple-wavelength optical coupler optically coupling said multiple-wavelength beam splitter to said first fiber optical device, and another optical coupler optically coupling said diagnostic radiation source to said second fiber optical device.

6. The system of claim 5 wherein at least one of said fiber optical devices is a single optical fiber.

7. The system of claim 5 wherein at least one of said fiber optical devices is a bundle of optical fibers.

8. The system of claim 1 wherein said fiberoptical means is a fiberoptical device having a central fiber optical diagnostic means with a proximal end coupled to said diagnostic radiation source, a receiving fiberoptical array means annularly disposed about said diagnostic means with a proximal end coupled to said detector, and a treatment fiber optical array also annularly disposed about said diagnostic means with one end coupled to said treatment laser source.

* * * * *